(12) United States Patent
Itoh

(10) Patent No.: US 7,947,225 B2
(45) Date of Patent: May 24, 2011

(54) AUTOMATED TEST TUBE CAP REMOVAL APPARATUS

(75) Inventor: Teruaki Itoh, Kumamoto (JP)

(73) Assignee: IDS Co., Ltd., Kumamoto (JP)

( * ) Notice: Subject to any disclaimer, the term of this patent is extended or adjusted under 35 U.S.C. 154(b) by 535 days.

(21) Appl. No.: 12/003,910

(22) Filed: Jan. 3, 2008

(65) Prior Publication Data

US 2008/0170967 A1 Jul. 17, 2008

(30) Foreign Application Priority Data

Jan. 15, 2007 (JP) .................. 2007-006029

(51) Int. Cl.
  *G01N 21/00* (2006.01)
  *G01N 31/00* (2006.01)
  *G01N 33/00* (2006.01)

(52) U.S. Cl. ............... 422/63; 422/65; 436/43; 436/47; 436/48

(58) Field of Classification Search .................. 422/63, 422/65; 436/47, 48
See application file for complete search history.

(56) References Cited

U.S. PATENT DOCUMENTS

| 5,161,436 A * | 11/1992 | Stevenson ............... 81/3.41 |
| 2005/0047966 A1* | 3/2005 | Itoh .................... 422/99 |
| 2005/0252342 A1* | 11/2005 | Itoh .................... 81/3.2 |

FOREIGN PATENT DOCUMENTS

| CN | 1590276 | 3/2005 |
| JP | 61-22537 | 2/1986 |
| JP | 63-131385 | 8/1988 |
| JP | 5-228379 | 9/1993 |
| JP | 6-50980 | 2/1994 |
| JP | 2005-88180 | 4/2005 |
| JP | 2005-271991 | 10/2005 |

OTHER PUBLICATIONS

Japanese Official Action & English translation (2007-006029) mailed Aug. 5, 2008.

* cited by examiner

*Primary Examiner* — Brian J Sines
(74) *Attorney, Agent, or Firm* — Nixon & Vanderhye P.C.

(57) ABSTRACT

A automated test tube cap removal apparatus includes, a cap remover, a test tube rack which holds a plurality of capped test tubes upright in a row, a clamping mechanism which is disposed in the cap removing position and clamps the plurality of test tubes, and a cap removal unit disposed in the cap removing position and configured to move upward to remove caps from some of a plurality of test tubes and move upward to remove caps from the remaining test tubes. The cap removal unit includes engaging members which are capable of advance and retreat with respect to the caps and clamp each cap, a lift mechanism which raises the engaging members while alternately moving the engaging members upward, thereby removing the cap from each test tube, a cap guide member which separates the cap and guides the cap for dropping.

5 Claims, 12 Drawing Sheets

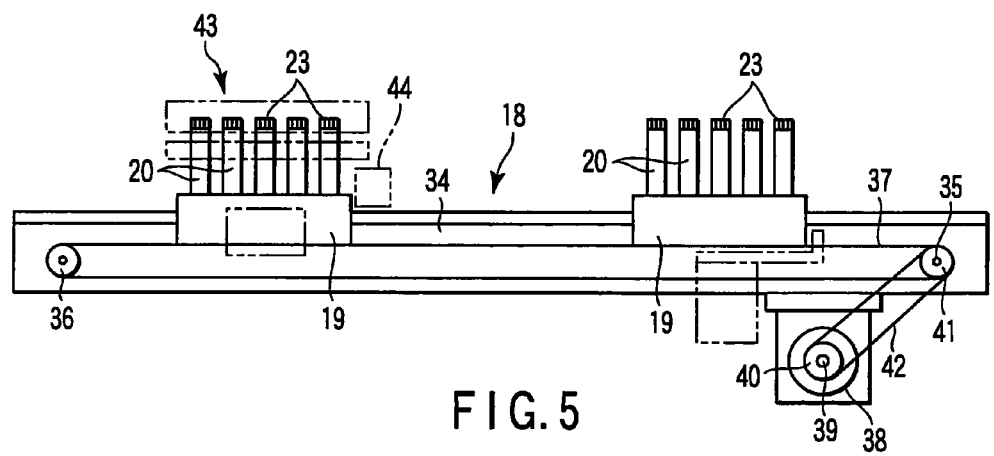
F I G. 5
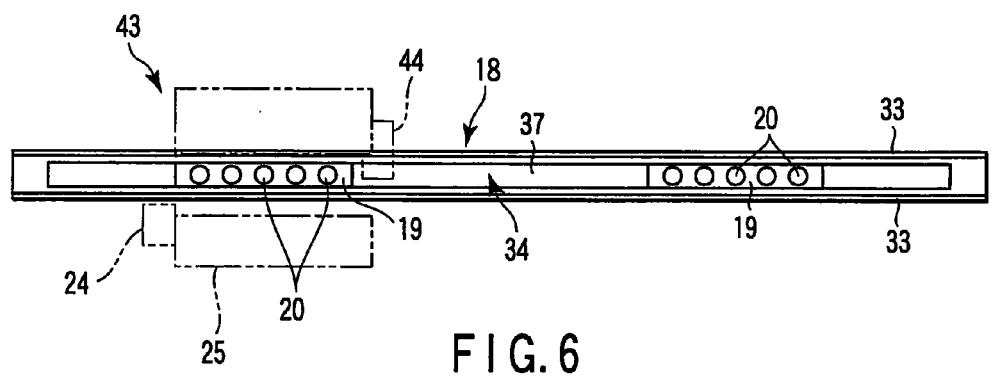
F I G. 6
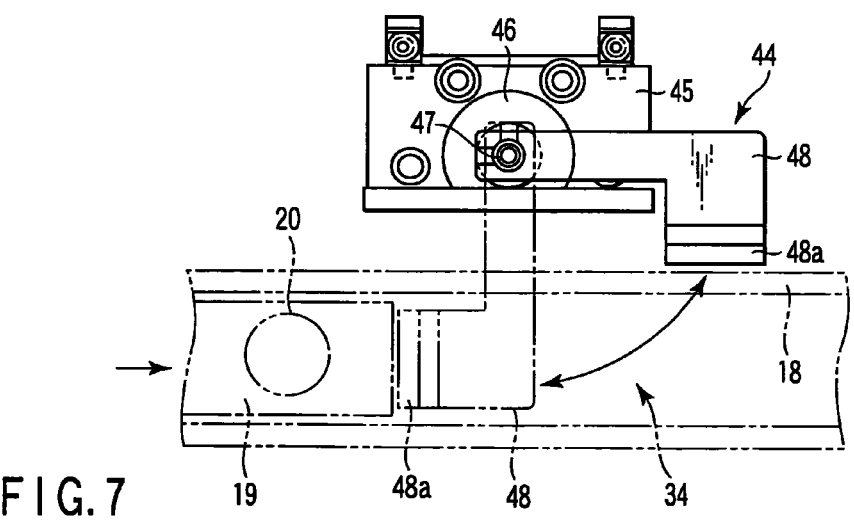
F I G. 7

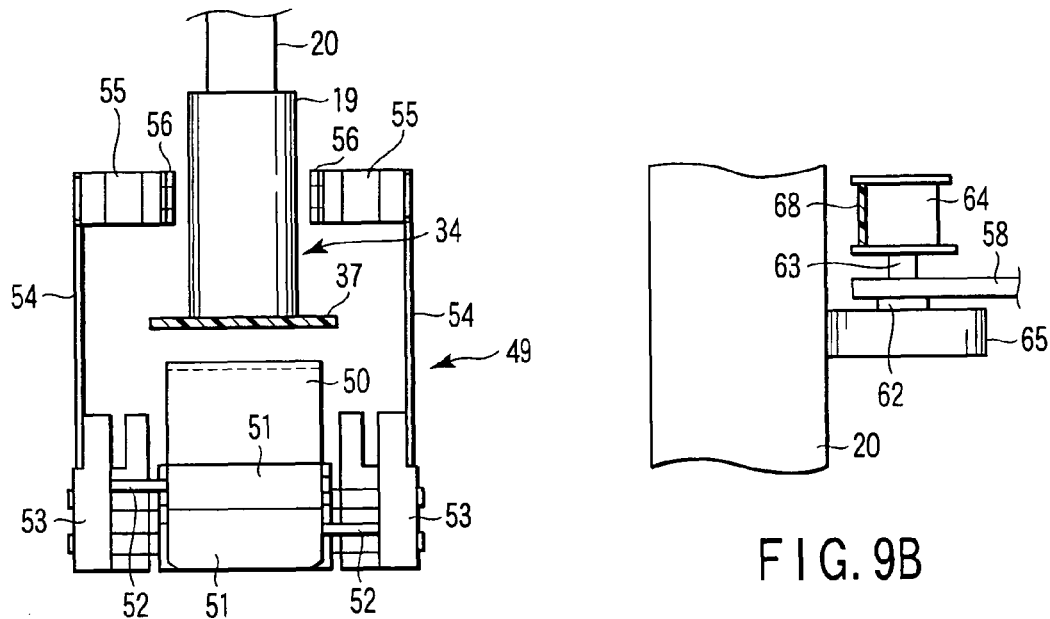
FIG. 8
FIG. 9B
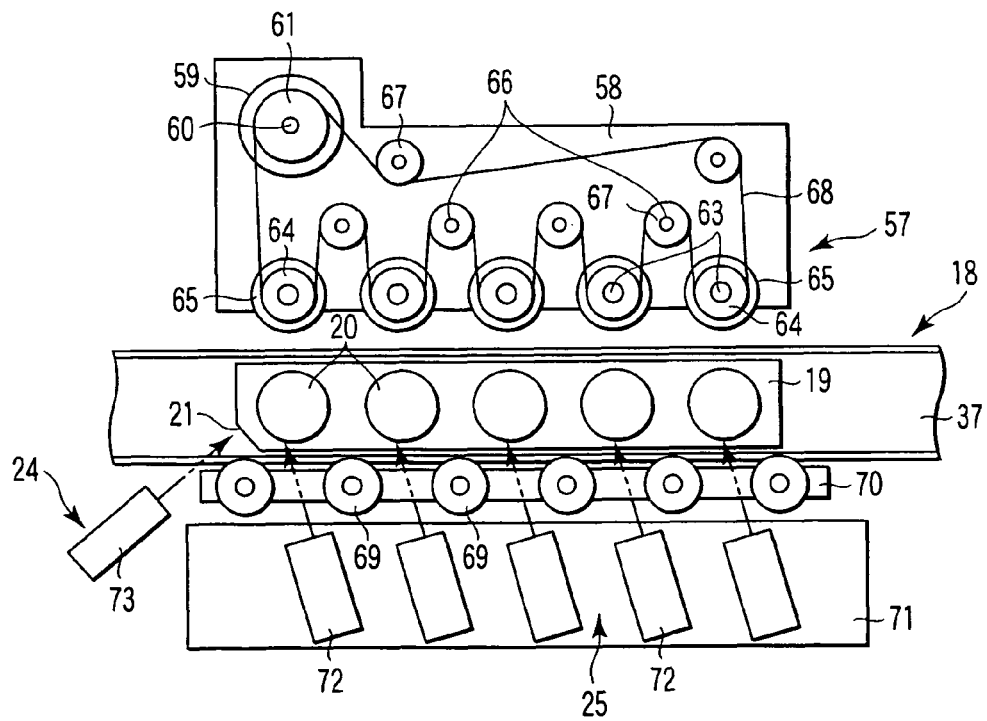
FIG. 9A

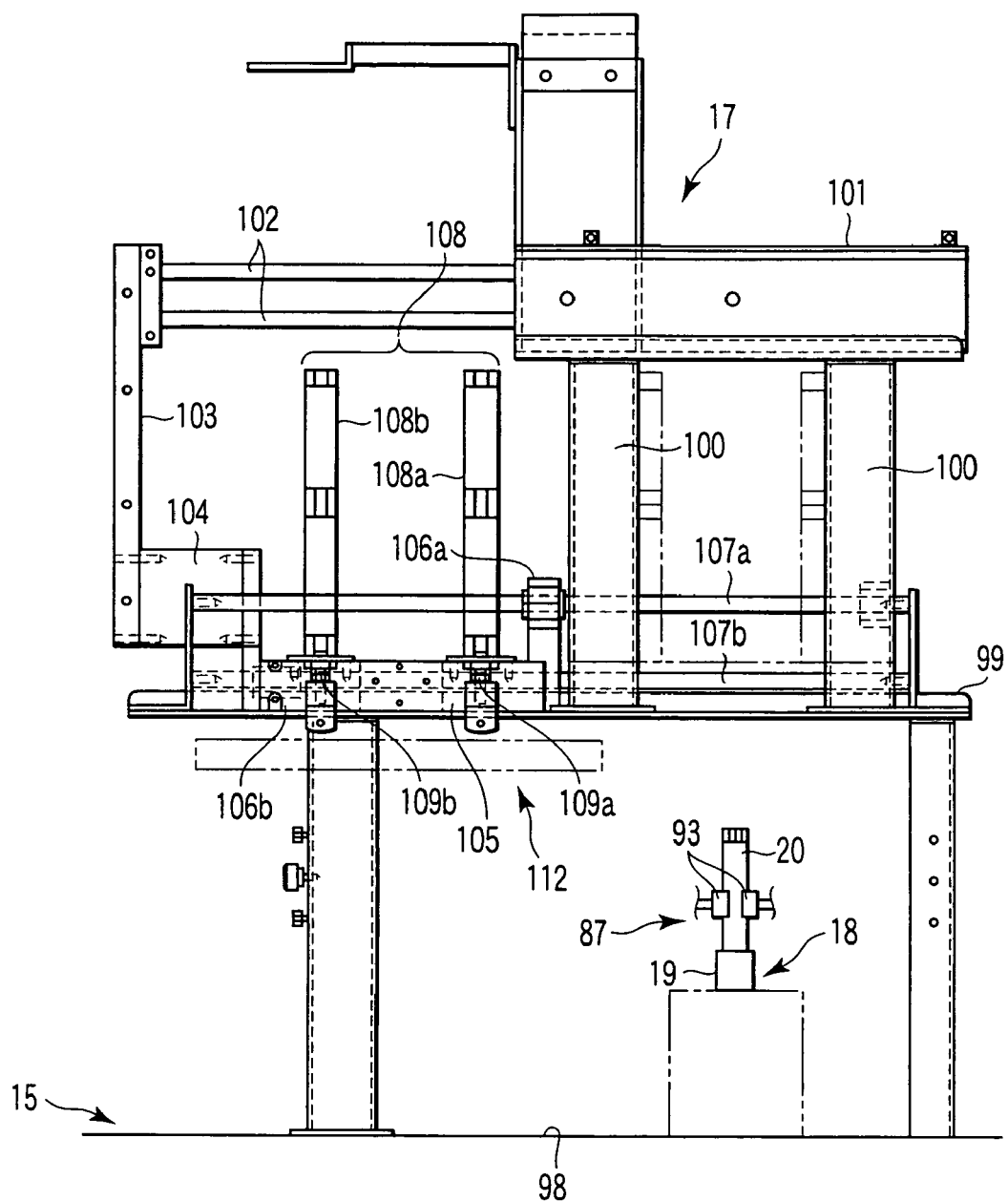
F I G. 15

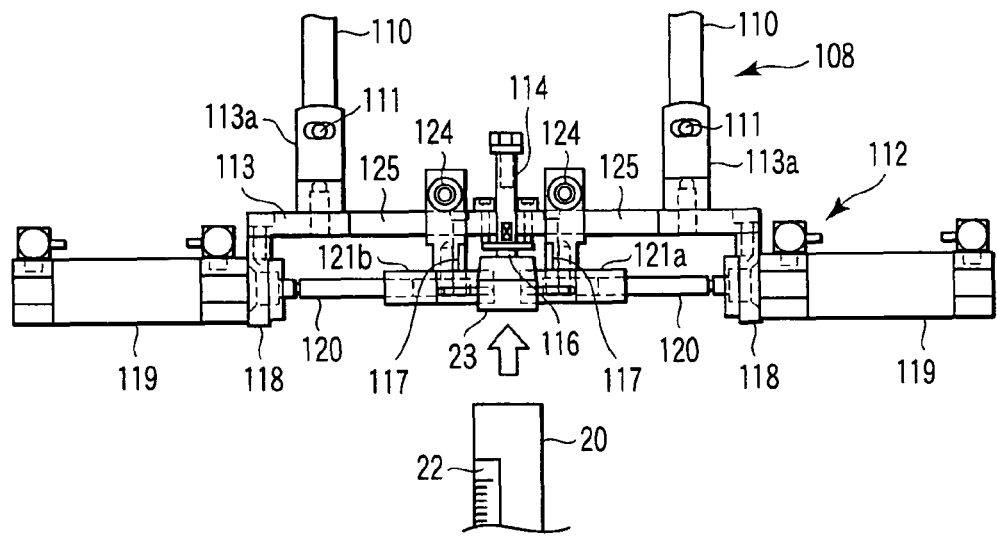
F I G. 18
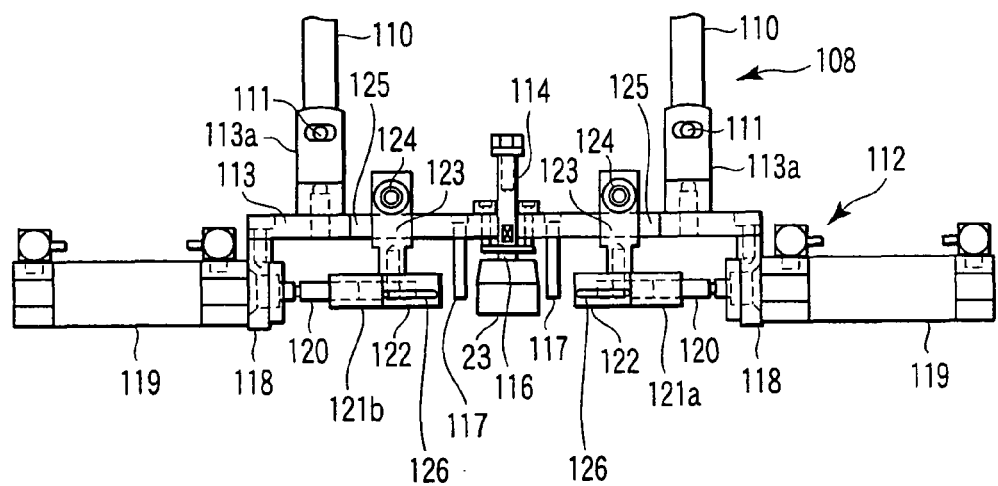
F I G. 19

AUTOMATED TEST TUBE CAP REMOVAL APPARATUS

CROSS-REFERENCE TO RELATED APPLICATIONS

This application is based upon and claims the benefit of priority from prior Japanese Patent Application No. 2007-006029, filed Jan. 15, 2007, the entire contents of which are incorporated herein by reference.

BACKGROUND OF THE INVENTION

1. Field of the Invention

This invention relates to an automated test tube cap removal apparatus for automatically removing caps from test tubes that contain a specimen, such as blood.

2. Description of the Related Art

In a known apparatus for removing caps from test tubes, as described in Jpn. Pat. Appln. KOKAI Publication No. 5-228379, for example, the cap of each test tube is supported by engagement with the distal end portion of a drawing arm in a manner such that the test tubes are held one by one by a test tube retaining member. Then, the drawing arm is raised in a cap drawing direction to automatically draw the cap from the test tube by actuating a lift cylinder with the cap supported by engagement.

The drawing arm has a cap engaging claw at its distal end and is configured to rock the arm-supported cap through a predetermined angular range around its axis in conjunction with a tilt guide as the arm is pulled up by the lift cylinder.

Another example of a known test tube cap removal apparatus is described in Jpn. Pat. Appln. KOKAI Publication No. 2005-271991. In this apparatus, a movable apparatus frame capable of up-and-down motion is disposed above a cap removal portion. A lift mechanism for the movable apparatus frame can lower a descent stop position of a cap engaging chuck from a cap engaging position for large-sized test tubes to a cap engaging position for small-sized test tubes.

The lift mechanism is provided with a vertical ball screw and a drive motor for actuating the screw. As the ball screw is actuated by the drive motor, the movable apparatus frame is moved up and down at strokes corresponding to the test tube size. The test tube is held by a clamping mechanism, and its cap is supported by engagement with a chuck mechanism as it is rotated and raised in a cap disengaging direction, whereby the cap is removed. Even though the test tube size varies or if caps of different types are fitted on the test tubes, therefore, the caps can be removed quickly and accurately from the test tubes.

There are test tubes of various sizes (tube diameters and tube lengths), typically including $\phi 13 \times 75$ mm, $\phi 13 \times 100$ mm, $\phi 16 \times 75$ mm, $\phi 16 \times 100$ mm, etc. Further, caps that close the respective openings of the test tubes may be of various types, such as rubber and plastic push-in caps.

However, the test tube cap removal apparatus described above is furnished with the test tube clamping mechanism located in a cap removing position in the middle of a conveying path for conveying each test tube that contains a specimen. When the test tube that is conveyed along the conveying path reaches the cap removing position, it is held by the clamping mechanism. As this is done, the chuck mechanism descends and supports the test tube cap by engagement. The cap is removed by raising the chuck mechanism in rotation in the cap disengaging direction.

Specifically, the test tubes being conveyed along the conveying path are held one by one as they are removed. In uncapping a large number of test tubes that are housed in alignment in, for example, a test tube rack, therefore, the test tubes in the rack must be transferred to the conveying path so that they are carried one after another into the cap removing position as they are uncapped. Thus, the efficiency of cap removal is low.

This invention has been made in consideration of these circumstances, and its object is to provide an automated test tube cap removal apparatus capable of simultaneously uncapping a plurality of aligned test tubes in a test tube rack at a stroke, thereby ensuring high-efficiency test tube cap removal.

BRIEF SUMMARY OF THE INVENTION

According to an aspect of the invention, an automated test tube cap removal apparatus comprises, a cap remover having a cap removing position for a test tube which contains a specimen, a test tube rack which holds a plurality of capped test tubes upright in a row and loads the test tubes into the cap removing position, a clamping mechanism which is disposed in the cap removing position and clamps the plurality of test tubes in the test tube rack, and a cap removal unit disposed in the cap removing position and configured to move upward to remove caps from some of a plurality of test tubes held in the test tube rack in a manner such that the caps are simultaneously supported by engagement and then move upward to remove caps from the remaining test tubes in a manner such that the caps are simultaneously supported by engagement. The cap removal unit includes a pair of engaging members which are capable of advancing and retreating with respect to the caps and laterally clamping each cap when advanced, a lift mechanism which raises the pair of engaging members while alternately moving the engaging members upward, thereby removing the cap from each test tube, and a cap guide member which separates the cap from the engaging members and guides the cap for dropping when the engaging members retract from the cap after the cap removal.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5 is a side view of the rack conveying path of the embodiment;

FIG. 6 is a plan view of the rack conveying path of the embodiment;

FIG. 7 is a plan view of a first rack stopper of the embodiment;

FIG. 8 is a side view of a rack fixing mechanism of the embodiment;

FIGS. 9A and 9B show the embodiment, in which FIG. 9A is a plan view of a test tube rotating mechanism, and FIG. 9B is a side view showing the relationship between a test tube and a rolling-contact roller;

FIG. 15 is a side view of a cap removal mechanism of the embodiment;

FIG. 18 is a front view of the cap removal unit of the embodiment;

FIG. 19 is a front view of the cap removal unit of the embodiment; and

DETAILED DESCRIPTION OF THE INVENTION

An embodiment of this invention will now be described with reference to the accompanying drawings.

Figure 1:
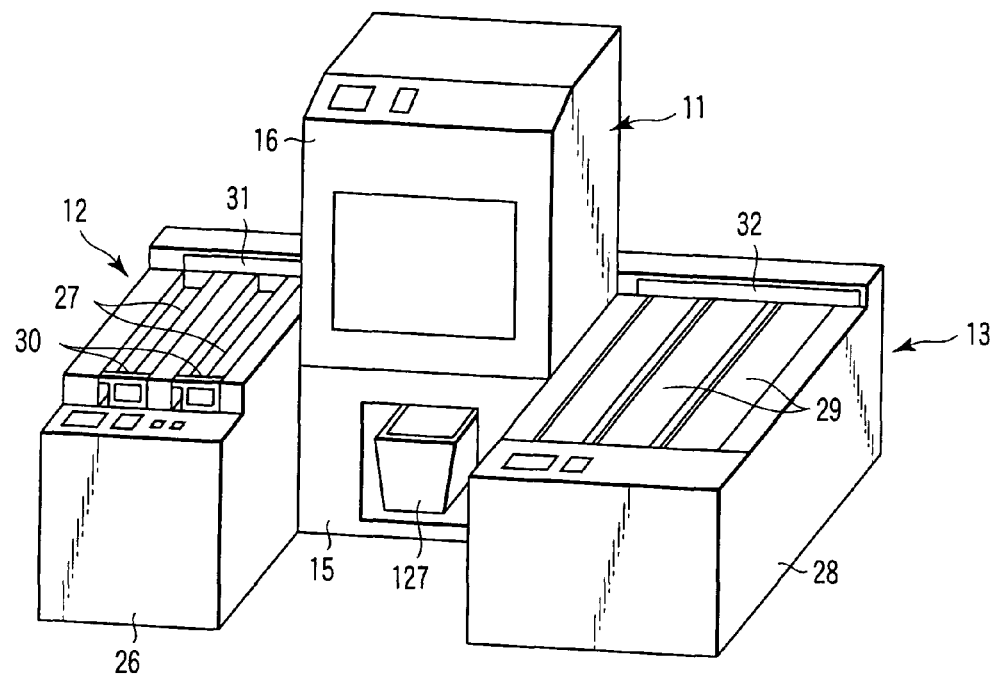
FIG. 1 is a perspective view of an automated test tube cap removal apparatus according to a first embodiment of the invention.
Figure 2:
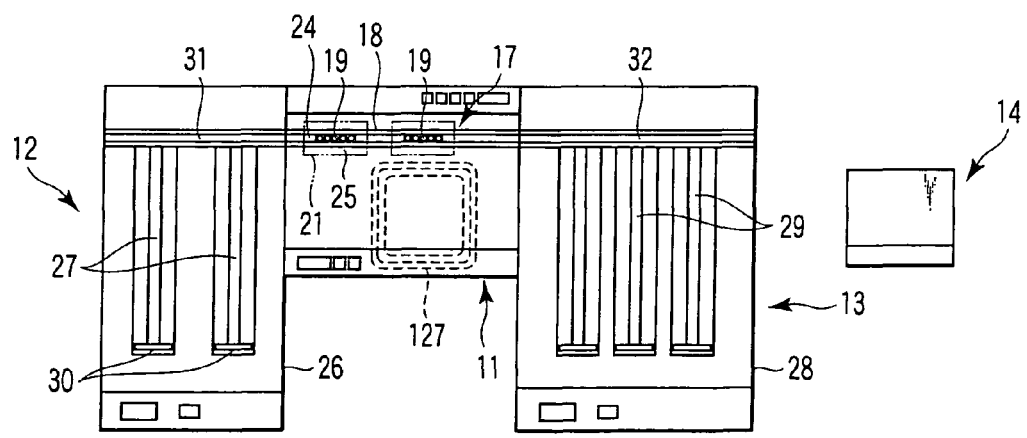
FIG. 2 is a plan view of the apparatus of the embodiment.

FIGS. 1 and 2 are a perspective view and a plan view, respectively, of an automated test tube cap removal apparatus. As shown in FIGS. 1 and 2, a cap remover 11 is provided in the central part of the apparatus. A start unit 12 for use as a test tube rack loading unit is set on the left-hand side of the cap remover 11, and a stocker unit 13 on the right-hand side. Further, a control unit 14 with a CPU is set near the start unit 12.

In the cap remover 11, a storage box 16 is disposed on top of a base 15, and a cap removal mechanism 17 (mentioned later) is located in the box 16. A rack conveying path 18 is provided at the rear part of the box 16. The conveying path 18 conveys test tube racks 19 that hold test tubes 20.

Figure 3:
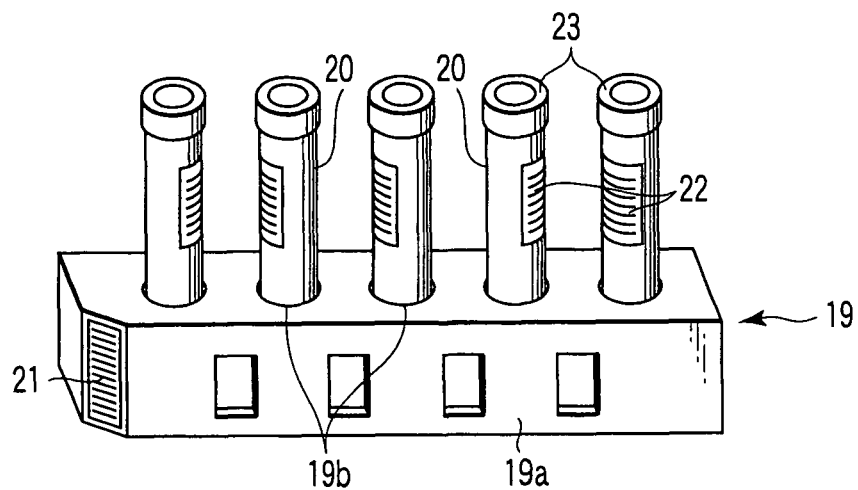
FIG. 3 is a perspective view of a test tube rack of the embodiment.

As shown in FIG. 3, each test tube rack 19 can hold a plurality of test tubes 20, five test tubes in a row, in an upright state. Specifically, the rack 19 is provided with insertion holes 19b in a top part of a laterally elongated rack body 19a such that the five test tubes 20 can be set upright in the holes, individually. Further, a rack barcode label 21 for rack identification is stuck on an end portion of the rack body 19a. Each test tube 20 contains a specimen, such as blood, and a test tube barcode label 22 for test tube identification is stuck on its side face. A cap 23 of rubber or synthetic resin is attached to an opening of each tube 20.

As shown in FIG. 2, moreover, the rack conveying path 18 at the rear part of the cap remover 11 is provided with first and second barcode readers 24 and 25. The first barcode reader 24 can read a barcode on the rack barcode label 21 of the test tube rack 19. The second barcode reader 25 simultaneously reads barcodes on the respective test tube barcode labels 22 of the individual test tubes 20. After the barcodes are read, the test tube rack 19 is conveyed to the cap removal mechanism 17.

A base 26 of the start unit 12 is as tall as the base 15 of the cap remover 11. Arranged on top of the base 26 are a plurality of rack trays 27 that contain a large number of test tube racks 19 in which capped test tubes 20 are held. Likewise, a base 28 of the stocker unit 13 is as tall as the base 15 of the cap remover 11. Arranged on top of the base 28 are a plurality of rack trays 29 that contain a large number of test tube racks 19 in which unstopped test tubes 20 and erroneously accepted test tubes 20 are held.

The rack trays 27 and 29 have basically the same construction in which the test tube racks 19 are arranged standing upright in a transverse row (in a direction perpendicular to the direction of arrangement of the test tubes 20). Further, the rack trays 27 of the start unit 12 are provided individually with pusher bars 30, which can push the test tube racks 19 toward a rack loading path 31, thereby successively loading the racks 19, the leading one first, into the path 31.

A rack unloading path 32 is provided at the rear part of the stocker unit 13. The downstream end of the rack loading path 31 is connected to the upstream end of the rack conveying path 18. Further, the upstream end of the rack unloading path 32 is connected to the downstream end of the conveying path 18. Thus, the loading and unloading paths 31 and 32 are coupled straight to the conveying path 18, so that the test tube racks 19 that contain the five test tubes 20 each can be conveyed along the paths.

Figure 4:
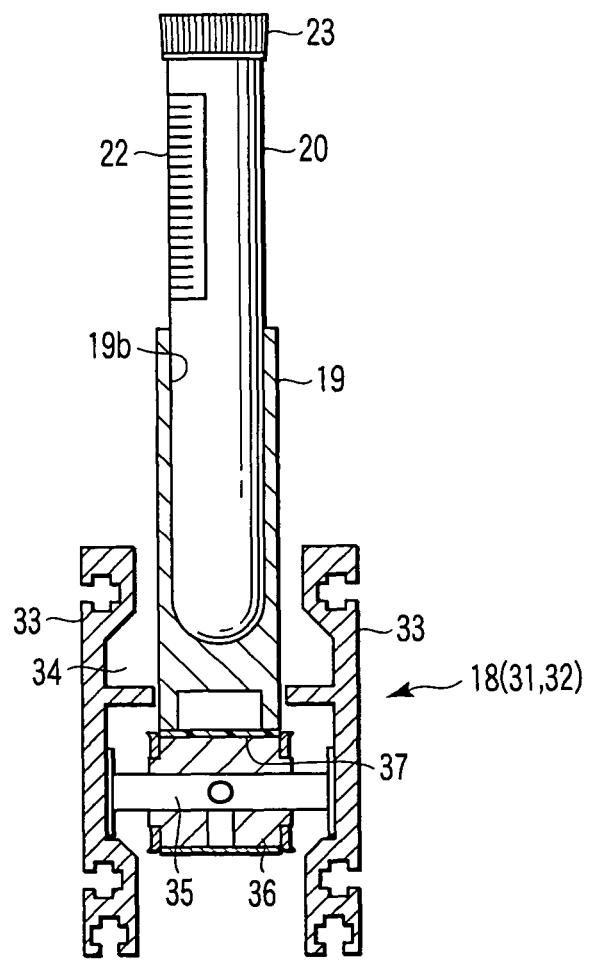
FIG. 4 is a cross-sectional view of a rack conveying path of the embodiment.

The rack conveying path 18 and the rack loading and unloading paths 31 and 32 have the same construction shown in FIG. 4. Specifically, an open-topped, square U-shaped channel 34 is defined by a pair of guide plates 33 that are arranged parallel to and spaced from each other. Rollers 36 on horizontal rotating shafts 35 are provided individually for rotation at the front and rear end portions of the channel 34 with respect to its longitudinal direction. An endless conveyor belt 37 is passed around and stretched between these rollers 36. The belt 37 is run in the longitudinal direction of the channel 34 by a drive mechanism, which will be mentioned later. Thus, the test tube racks 19 can be placed on the conveyor belt 37 and conveyed along the channel 34.

As shown in FIGS. 5 and 6, a drive motor 38 is fixed to the base 15 under the rack conveying path 18 in a manner such that its rotating shaft 39 is kept horizontal. A driving pulley 40 is fitted on the shaft 39 of the motor 38. The rotating shaft 35 of one of the rollers 36 projects horizontally, and a driven pulley 41 is fitted on the shaft 35. A belt 42 is passed around and stretched between the driving and driven pulleys 40 and 41 so that the rotation of the drive motor 38 is transmitted to the conveyor belt 37 by the belt 42.

The following is a description of a barcode reader section 43 that includes the first and second barcode readers 24 and 25. A first rack stopper 44 is provided at the front part of the barcode reader section 43. It serves to temporarily stop each test tube rack 19 that is conveyed along the rack conveying path 18. As shown in FIG. 7, the first rack stopper 44 is provided with a bracket 45 that is fixed to the base 15. A rotary actuator 46 is fixed to the bracket 45 in a manner such that its rotating shaft 47 extends vertically. The shaft 47 is fitted with an L-shaped stopper piece 48 that has a gel tip 48a on its distal end portion. The stopper piece 48 can be rocked through about 90 degrees in the direction of the arrow by the rotary actuator 46. In stopping each test tube rack 19, the gel tip 48a projects into the channel 34, as indicated by two-dot chain line. When the rack 19 is expected to be passed, the tip 48a is retracted from the channel 34, as indicated by solid line.

Further, a rack fixing mechanism 49 for temporarily fixing each test tube rack 19 is provided under the rack conveying path 18 corresponding to the barcode reader section 43. As shown in FIG. 8, the fixing mechanism 49 is provided with a cylinder bracket 50 that is fixed to the base 15. The bracket 50 is provided with a pair of air cylinders 51 that extend parallel to each other in a manner such that their corresponding piston rods 52 project in opposite directions (in the transverse direction of the conveying path 18). Arm bases 54 are disposed on the respective distal end portions of the paired piston rods 52 with the aid of mounting pieces 53, individually, and opposite chuck bases 55 are provided on the bases 54, individually. Further, the chuck bases 55 are provided individually with rubber chucks 56, which laterally hold and fix the test tube rack 19.

Figure 10:
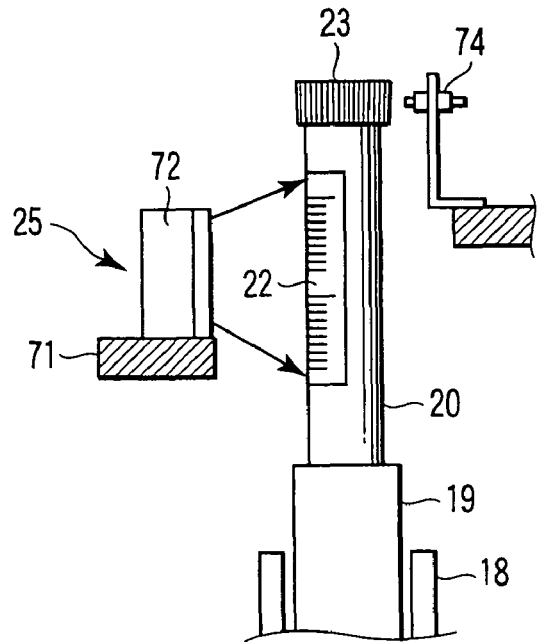
FIG. 10 is a side view showing the relationship between the test tube and a second barcode reader.

Furthermore, the barcode reader section 43 is provided with a test tube rotating mechanism 57. The rotating mechanism 57 is configured to rotate the test tubes 20 in each test tube rack 19 so that the second barcode reader 25 can read the barcode on each test tube barcode label 22 without regard to the position of the label 22. More specifically, as shown in FIGS. 9A, 9B and 10, the test tube rotating mechanism 57 is provided with a motor bracket 58 that is fixed to the base 15. The bracket 58 is horizontally disposed at a height near the upper end portion of each test tube 20 held in the test tube rack 19. A drive motor 59 is fixed to the motor bracket 58 in a manner such that its rotating shaft 60 extends vertically, and a driving pulley 61 is fitted on the shaft 60. At one side edge portion of the bracket 58, five bearings 62 are provided on the channel 34 side of the rack conveying path 18. Vertical shafts 63 are supported individually by these bearings 62, and a driven pulley 64 and a rolling-contact roller 65 are fitted on the upper and lower end portions, respectively, of each of the shafts 63.

Six vertical shafts 66 are supported individually by bearings on the opposite side of the motor bracket 58 from the channel 34, and guide pulleys 67 are fitted individually on the respective upper end portions of the shafts 66. A timing belt 68 is windingly passed around and stretched between the driving pulley 61, driven pulleys 64, and guide pulleys 67.

On the opposite side of the channel 34 from the motor bracket 58, six receiving rollers 69 are rotatably supported on a roller support member 70. These receiving rollers 69 are set opposite the respective side faces of the test tubes 20. They can support the tubes 20 lest the tubes tilt when subjected to a pressing force of the rolling-contact rollers 65. Thus, the five test tubes 20 held in the test tube rack 19 are supported in a vertical state by the receiving rollers 69 when the five rolling-contact rollers 65 on the channel 34 side rotate to apply a rotational force to the tubes 20 in rolling contact therewith.

A mounting base 71 is provided on the opposite side of the channel 34 from the test tube rotating mechanism 57 constructed in this manner. The mounting base 71 is provided with five inclined reader bodies 72, which individually face the respective barcode labels 22 of the five test tubes 20 in the test tube rack 19. Further, a reader body 73 of the first barcode reader 24 is disposed beside the mounting base 71 so as to face the test tube rack 19. In FIG. 10, number 74 denotes a sensor that detects the presence of the cap 23 of each test tube 20.

Figure 11:
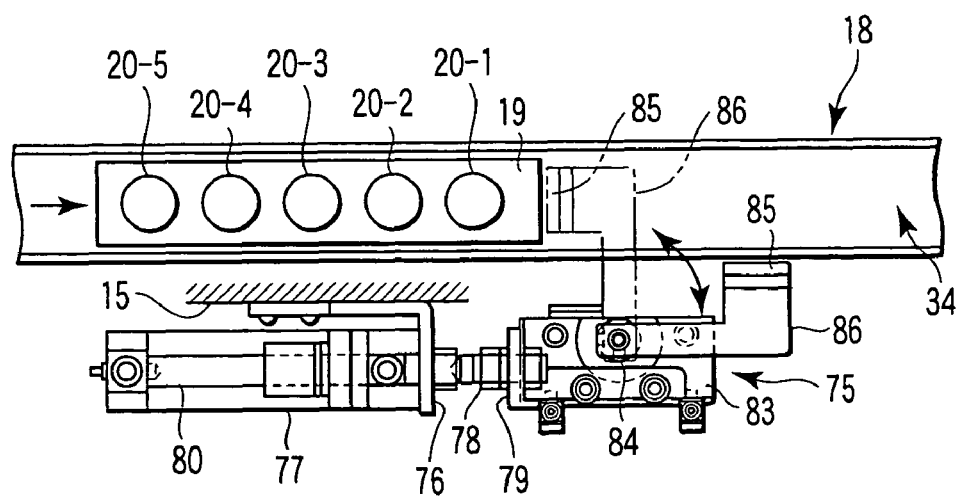
FIG. 11 is a plan view of a second rack stopper of the embodiment.
Figure 12:
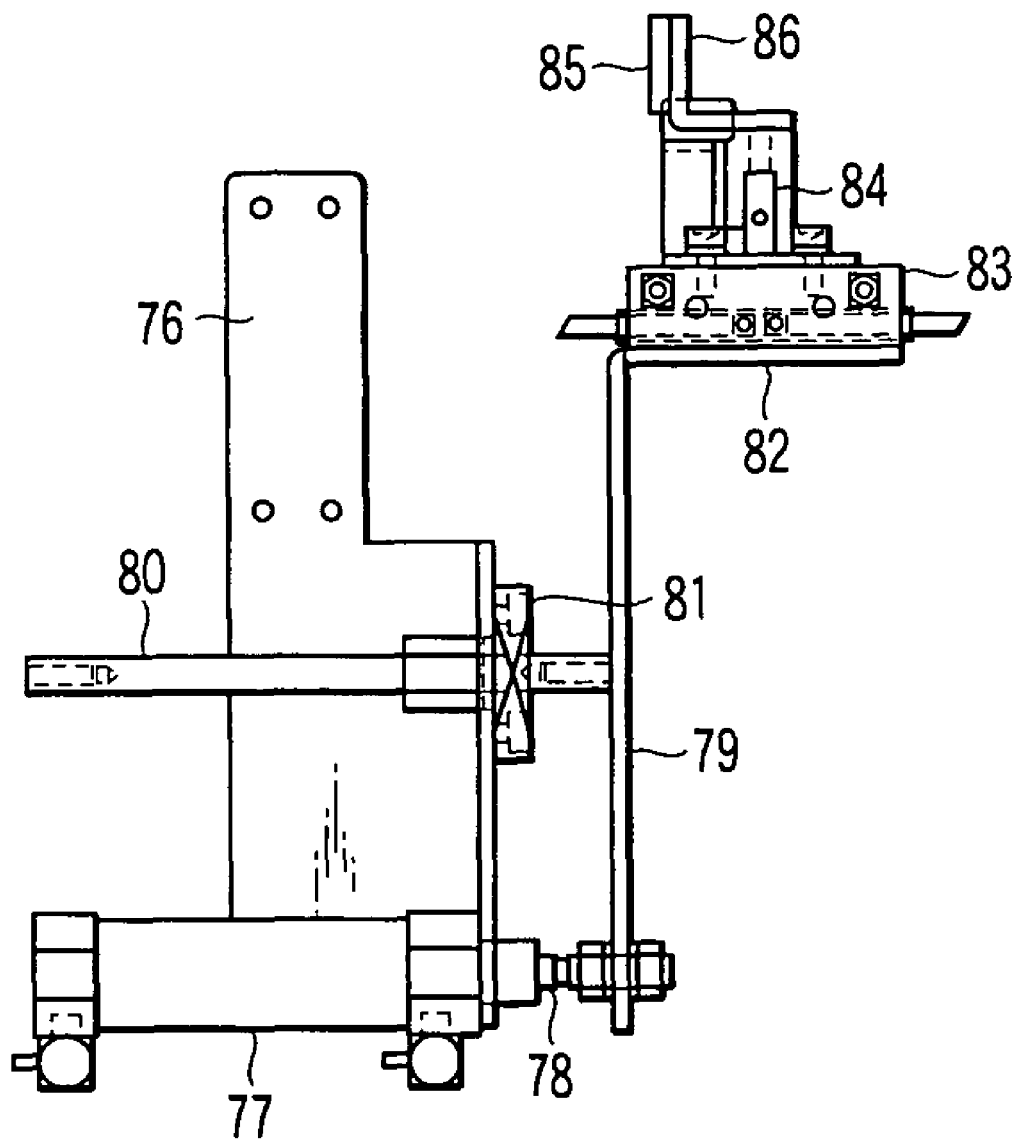
FIG. 12 is a side view of the second rack stopper of the embodiment.

The following is a description of the cap removal mechanism 17. The mechanism 17 is provided with a second rack stopper 75 that temporarily stops the test tube rack 19 conveyed by the rack conveying path 18 in a cap removing position. As shown in FIGS. 11 and 12, the second rack stopper 75 is provided with a cylinder bracket 76 that is fixed to the base 15. An air cylinder 77 is fixed to the bracket 76 in a manner such that its piston rod 78 extends parallel to the rack conveying path 18 in the conveying direction thereof. An actuator bracket 79 is fixed to the distal end portion of the piston rod 78. An LM guide 80 is fixed to the actuator bracket 79, and an LM bush 81 that is attached to the bracket 79 is slidably supported by the guide 80. The actuator bracket 79 is movable between two positions, an advanced position and a retracted position, in the conveying direction of the rack conveying path 18.

An L-shaped mounting portion 82 is provided on the upper end portion of the actuator bracket 79. A rotary actuator 83 is fixed to the mounting portion 82 in a manner such that its rotating shaft 84 extends vertically. The shaft 84 is fitted with an L-shaped stopper piece 86 that has a gel tip 85 on its distal end portion. The stopper piece 86 can be rocked through about 90 degrees in the direction of the arrow by the rotary actuator 83. In stopping each test tube rack 19 that is conveyed along the rack conveying path 18, the gel tip 85 projects into the channel 34, as indicated by two-dot chain line. When the rack 19 is expected to be passed, the tip 85 is retracted from the channel 34, as indicated by solid line.

Further, the cap removal mechanism 17 performs two stages of cap removal in the following manner. It first removes caps from the first, third, and fifth test tubes 20 (denoted by numbers 20-1, 20-3 and 20-5 in FIG. 11) as viewed in the conveying direction, among the five test tubes 20 supported by the test tube rack 19, as described later. Then, the mechanism 17 removes the remaining second and fourth test tubes 20 (denoted by numbers 20-2 and 20-4). Thus, in the first stage of cap removal, the test tube rack 19 is stopped when the first, third, and fifth test tubes 20 are located in the cap removing position with the actuator bracket 79 retracted, as shown in FIG. 11. In the second stage of cap removal, the test tube rack 19 can be stopped when the second and fourth test tubes 20 are located in the cap removing position with the bracket 79 advanced by the air cylinder 77.

Figure 13:
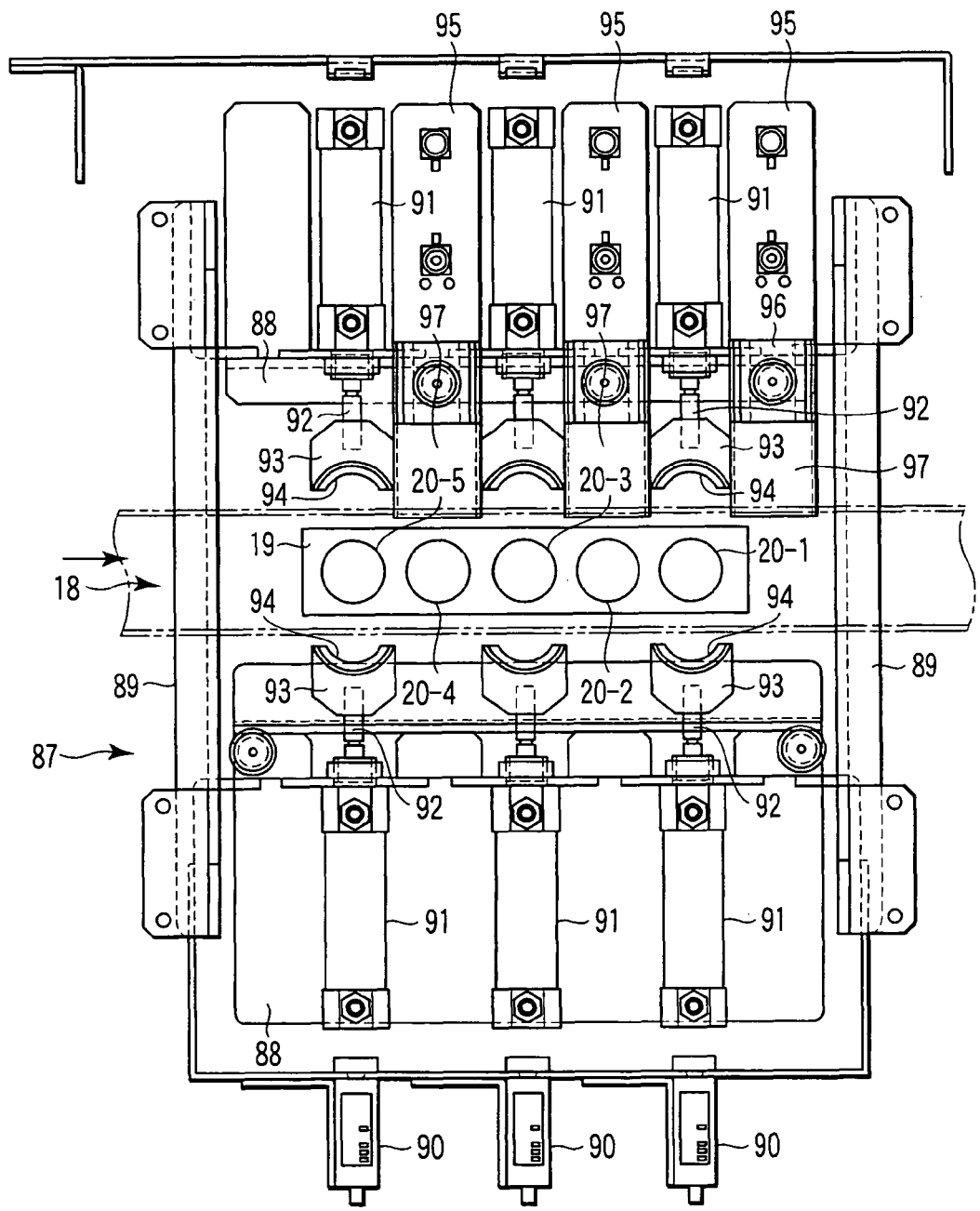
FIG. 13 is a plan view of a test tube clamping mechanism of the embodiment.
Figure 14:
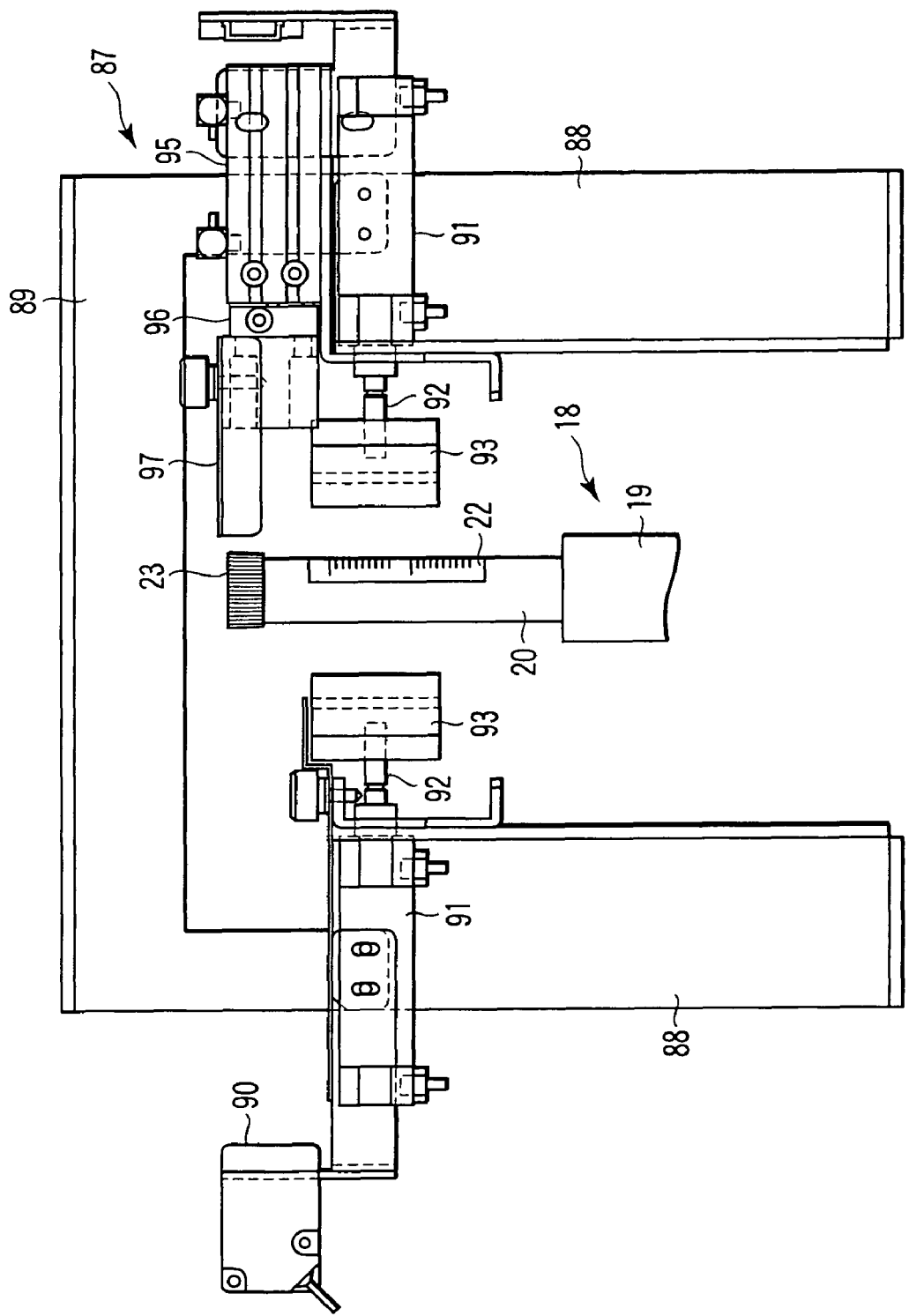
FIG. 14 is a side view of the test tube clamping mechanism of the embodiment.
Figure 16:
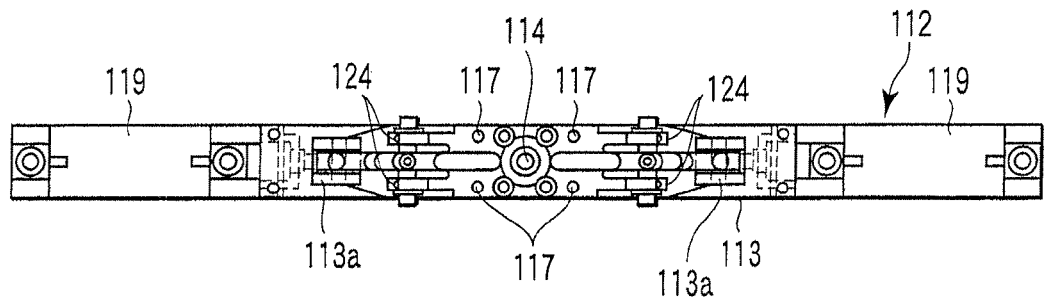
FIG. 16 is a plan view of a cap removal unit of the embodiment.
Figure 17:
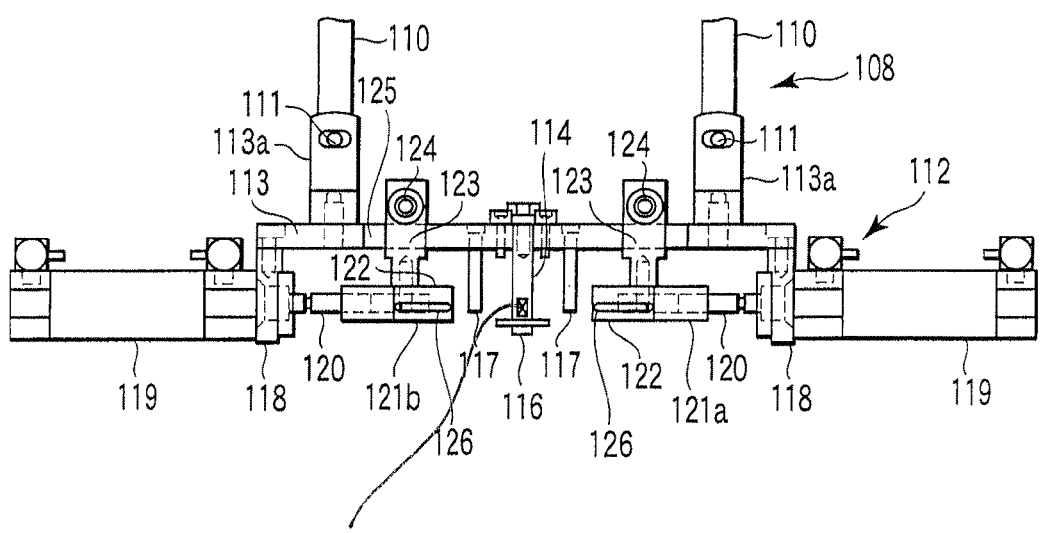
FIG. 17 is a front view of the cap removal unit of the embodiment.
Figure 20:
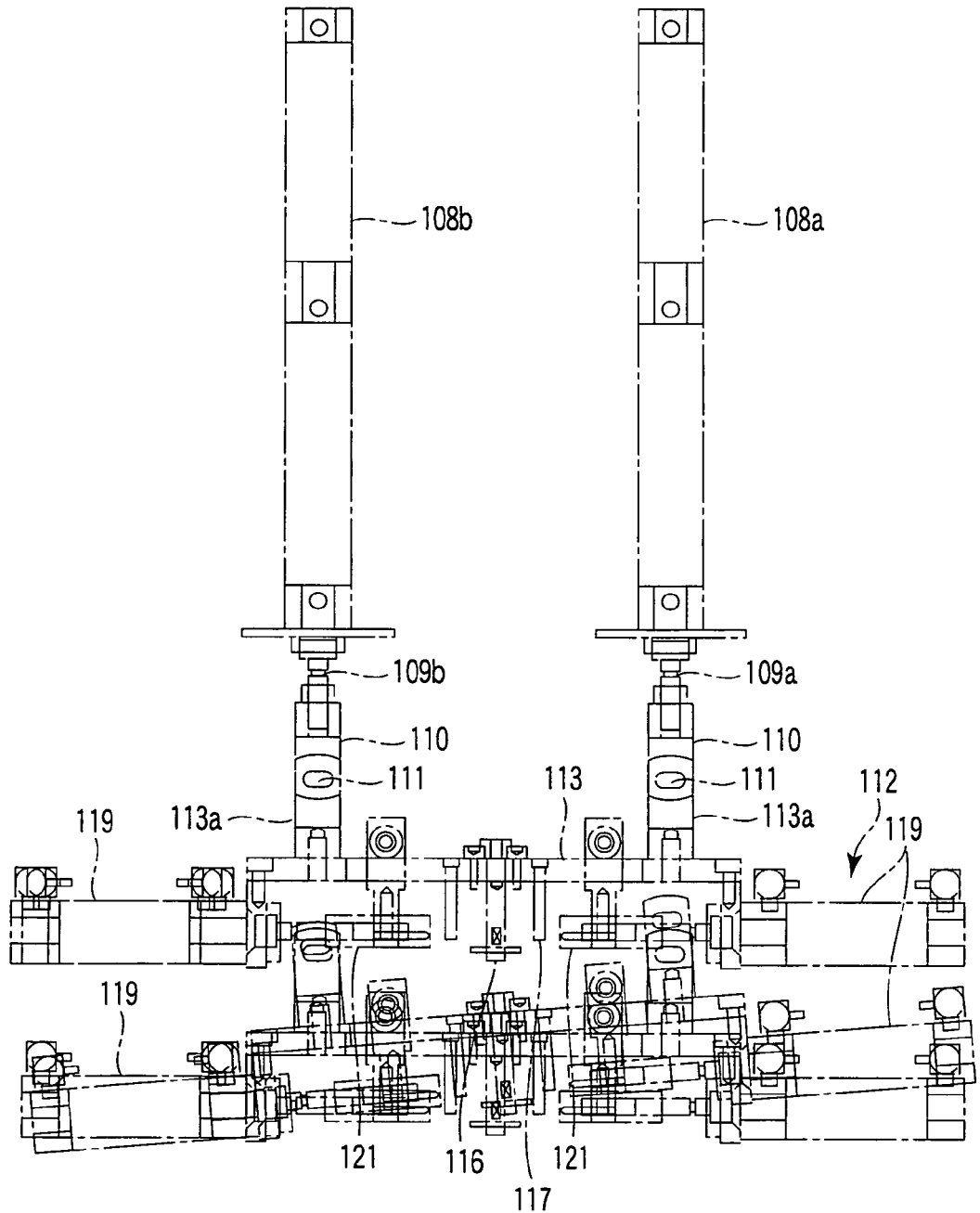
FIG. 20 is a front view showing the operation of the cap removal unit of the embodiment.

Furthermore, the cap removal mechanism 17 is provided with a test tube clamping mechanism 87 that clamps the test tubes 20 supported by the test tube rack 19 when the test tubes are to be uncapped. In the clamping mechanism 87, as shown in FIGS. 13 and 14, a pair of cylinder bases 88 are opposed to each other with the rack conveying path 18 between them. A sensor bracket 89 is stretched between the bases 80 so as to bridge the rack conveying path 18. The sensor bracket 89 is provided with three test tube sensors 90 that are arranged at regular intervals. The sensors 90 individually face the first, third, and fifth test tubes 20-1, 20-3 and 20-5 as viewed in the conveying direction, among the five test tubes 20 supported by the test tube rack 19, when the rack 19 is stopped in the cap removing position, and detect the presence of the test tubes 20.

The pair of cylinder bases 88 are provided with three pairs of air cylinders 91, which, like the test tube sensors 90, individually face the first, third, and fifth test tubes 20-1, 20-3 and 20-5 as viewed in the conveying direction, among the five test tubes 20 supported by the test tube rack 19. The air cylinders 91 are arranged at regular intervals and face one another with the rack conveying path 18 between them. Each air cylinder 91 is provided with a piston rod 92, which can advance toward and retreat from the rack conveying path 18, and a clamping piece 93 is attached to the distal end portion of each piston rod 92. The clamping piece 93 is in the shape of a semicircle along the contour of each test tube 20. A rubber pad 94 is stuck on the inner peripheral surface of each clamping piece 93 so that the pieces 93 can clamp and fixedly hold the trunk of the test tube 20 from both sides.

As shown in FIG. 13, one (on the right-hand side of FIG. 14) of the paired cylinder bases 88 is provided with three shutter cylinders 95 that extend parallel to one another adjoining the air cylinders 91. Respective piston rods 96 of these shutter cylinders 95 can advance toward and retreat from the rack conveying path 18, and a shutter 97 is fixed to each piston rod 96. The shutter 97 has an inverted U-shaped cross section. It serves to cover a region around an opening portion including the top opening of each test tube 20 when advanced, thereby preventing foreign matter or the like from getting into the adjacent uncapped test tube 20 through its opening when each test tube 20 is uncapped.

The following is an additional description of the cap removal mechanism 17. As shown in FIG. 15, the base 15 is provided with a support plate 98 that supports the rack conveying path 18. A support block 99 is provided on the support plate 98 so as to bridge the rack conveying path 18. Further, a pair of props 100 are set up on top of the support block 99 so as to be spaced in the longitudinal direction of the cap removal mechanism 17. Three parallel twin-rod cylinders 101 are fixed horizontally on the respective upper end portions of the pair of props 100. Twin rods 102 of the twin-rod cylinders 101 project in the longitudinal direction of the cap removal mechanism 17 (perpendicular to the rack conveying path 18).

A vertical connecting member 103 is fixed to the distal end portion of each twin rod 102, and a moving block 105 is attached to the connecting member 103 by a bracket 104. Each moving block 105 is provided with LM blocks 106a and 106b, which are guided by LM rods 107a and 107b, respectively, for movement in the longitudinal direction of the cap removal mechanism 17. Specifically, the moving block 105 is configured to reciprocate between a cap removing position P1 and a cap disposal position P2.

A couple of vertical two-stage cylinders 108a and 108b that constitute a lift mechanism 108 are fixed individually to the opposite end portions of each moving block 105 with their respective piston rods 109a and 109b facing downward. The two-stage cylinders 108a and 108b are dual-stroke cylinders in which the piston rods 109a and 109b alternately ascend by 10 mm with a time difference in a first stage and simultaneously ascend by 40 mm in a second stage, for example.

Cap removal units 112 are tiltably coupled to the respective lower end portions of the piston rods 109a and 109b of the two-stage cylinders 108a and 108b by knuckle joints 110 and joint shafts 111, individually. One cap removal unit 112 is provided for each moving block 105 that is driven by each of the three twin-rod cylinders 101. Therefore, three units 112 are arranged at regular intervals in the conveying direction of the rack conveying path 18. Each of these intervals is adjusted to a pitch between each two alternately adjacent ones of the five test tubes 20 supported by the test tube rack 19.

Each cap removal unit 112 is constructed in the manner shown in FIGS. 16 to 20. Specifically, a support plate 113 has a rectangular shape, and hangers 113a on the opposite end portions of the support plate 113 are supported in a horizontal state by their corresponding knuckle joints 110 and joint shafts 111. A cap retaining pin 114 is vertically penetratingly fixed to a longitudinally middle part of the support plate 113. A cap retaining member 116 is attached to the pin 114 with the aid of a coil spring 115. Further, four cap guide members 117 protrude downward from the support plate 113 so as to surround the pin 114. The guide members 117 are arranged at regular intervals around the retaining member 116. Each of these intervals is shorter than the outside diameter of each cap 23.

Mounting brackets 118 are fixed individually to the longitudinally opposite end portions of the support plate 113. Air cylinders 119 are horizontally fixed to the brackets 118 so as to face each other. Thus, piston rods 120 of the air cylinders 119 are movable with respect to the cap retaining member 116. A pair of engaging members 121a and 121b are fixed individually to the respective distal end portions of the piston rods 120.

The pair of engaging members 121a and 121b are spaced narrower than the pair of cap guide members 117. They are provided individually with circular arcuate recessed portions 122 such that they can advance between the guide members 117 to hold each cap 23 from both sides. The engaging members 121a and 121b are provided individually with upwardly projecting guide bars 123, which individually support guide rollers 124 for rotation with the aid of bearings. The support plate 113 is provided with guide holes 125 in its longitudinal direction. The guide bars 123 are configured to project above the support plate 113 through the guide holes 125 so that the guide rollers 124 can roll on the upper surface of the plate 113.

The respective recessed portions 122 of the engaging members 121a and 121b are provided individually with needle pins 126, which project toward the cap retaining member 116. The pins 126 are configured to be thrust into the side of each cap 23, thereby securely holding the cap 23, when the engaging members 121a and 121b advance to the retaining member 116 so that the recessed portions 122 engage and hold the cap 23 from both sides.

The following is a description of the operation of the automated test tube cap removal apparatus constructed in this manner.

A large number of test tube racks 19 are held in each rack tray 27 of the start unit 12, and five upright test tubes 20 are held in a row in each rack 19. When the pusher bars 30 of the start unit 12 are actuated to push the test tube racks 19 toward the rack loading path 31, the racks 19 are successively loaded into the path 31, the leading one first. The test tube racks 19 loaded in from the rack loading path 31 are placed on the conveyor belt 37 of the rack conveying path 18 and conveyed along the channel 34 to the barcode reader section 43.

The barcode reader section 43 is provided with the first and second barcode readers 24 and 25. When one of the test tube racks 19 reaches the barcode reader section 43, the first rack stopper 44 is actuated. More specifically, when the rotary actuator 46 is actuated to rotate the rotating shaft 47, the stopper piece 48 rocks through about 90 degrees, as indicated by two-dot chain line in FIG. 7, whereupon the gel tip 48a projects into the channel 34, as indicated by two-dot chain line. Thus, the test tube rack 19 that is conveyed along the rack conveying path 18 abuts the gel tip 48a and stops.

When the test tube rack 19 stops, the pair of air cylinders 51 of the rack fixing mechanism 49 are simultaneously actuated to withdraw the piston rods 52, so that the chuck bases 55 on the arm bases 54 move toward each other. Thereupon, the chuck bases 55 cause the rubber chucks 56 to laterally hold and fix the rack 19. As this is done, the conveyor belt 37 of the rack conveying path 18 is running. Since the test tube rack 19 is fixed by the rack fixing mechanism 49, however, it is bound to slip with respect to the belt 37.

On the other hand, the drive motor 59 of the test tube rotating mechanism 57 of the barcode reader section 43 is driven at this point in time, the driving pulley 61 rotates so that the timing belt 68 runs guided by the guide pulleys 67. Accordingly, the five rolling-contact rollers 65 that are supported by the motor bracket 58 rotate, so that the five test tubes 20 held in the rack 19 rotate in rolling contact with the rollers 65. Since the test tubes 20 are supported by the receiving rollers 69 when this is done, they can rotate in a vertical state without tilting.

On the opposite side of the channel 34 from the test tube rotating mechanism 57, the first barcode reader 24 faces the barcode label 21 of each test tube rack 19, while the second barcode reader 25 face the respective barcode labels 22 of the five test tubes 20 in the rack 19. Therefore, the respective types of the rack 19 and the tubes 20 can be read simultaneously.

When the types of the test tube rack 19 and the test tubes 20 are read in the barcode reader section 43, the pair of air cylinders 51 of the rack fixing mechanism 49 are simultaneously actuated to project the piston rods 52, so that the chuck bases 55 move away from each other. Accordingly, the chuck bases 55 leave the side face of the test tube rack 19, thereby releasing the rack 19 from fixation. At the same time, the rotary actuator 46 of the first rack stopper 44 is actuated to rotate the rotating shaft 47, and the stopper piece 48 rocks through about 90 degrees, whereupon the gel tip 48a is retracted from the channel 34, as indicated by solid line in FIG. 7. Thus, the test tube rack 19 is released and conveyed to the cap removal mechanism 17 in the next stage by the rack conveying path 18.

The cap removal mechanism 17 is provided with the second rack stopper 75 that temporarily stops the test tube rack 19 conveyed by the rack conveying path 18 in the cap removing position. The actuator bracket 79 of the stopper 75 is movable between the two positions, the advanced position and the retracted position, in the conveying direction of the rack conveying path 18.

First, if the rotary actuator 83 is actuated when the actuator bracket 79 is in the retracted position, the stopper piece 86 rocks through about 90 degrees, whereupon the gel tip 85 projects into the channel 34, as indicated by two-dot chain line in FIG. 11. Thus, the test tube rack 19 that is conveyed along the rack conveying path 18 abuts the gel tip 85 and stops.

When the test tube rack 19 stops, the first, third, and fifth test tubes 20-1, 20-3 and 20-5 as viewed in the conveying direction, among the five test tubes 20 supported by the test tube rack 19, are located in the cap removing position. Then, the presence of the test tubes 20 is detected by the three test tube sensors 90.

The three pairs of air cylinders 91, which, like the test tube sensors 90, individually face the first, third, and fifth test tubes 20-1, 20-3 and 20-5 as viewed in the conveying direction, among the five test tubes 20 supported by the test tube rack 19, are simultaneously actuated to project the piston rods 92. Thus, the respective clamping pieces 93 of the piston rods 92 clamp and fix the trunk of the test tube 20 from both sides.

When the three test tubes 20-1, 20-3 and 20-5 in the test tube rack 19 are fixed, the cap removal units 112 that individually face these tubes are simultaneously actuated to remove their caps.

Thus, when the cap removal units 112 are lowered by the agency of the two-stage cylinders 108a and 108b, the cap retaining pin 114 abuts the upper surface of each of the respective caps 23 of the test tubes 20-1, 20-3 and 20-5. When the cap removal units 112 are further lowered by the two-stage cylinders 108a and 108b, the pin 114 ascends compressing the coil spring 115, so that the cap 23 is pressed downward by the urging force of the spring 115.

When the respective air cylinders 119 of the cap removal units 112 in this state are simultaneously actuated to project the piston rods 120, the engaging members 121a and 121b on the respective distal end portions of the piston rods 120 advance toward the cap 23 of the test tube 20. Since the engaging members 121a and 121b are spaced narrower than the pair of cap guide members 117, they advance between the guide members 117 to hold each cap 23 from both sides. Since the engaging members 121a and 121b are provided individually with the projecting needle pins 126, moreover, the pins 126 are thrust into the side of the cap 23, thereby securely holding the cap 23, when the engaging members 121a and 121b are fitted on and hold the cap 23 from both sides.

Subsequently, if the one two-stage cylinder 108a, out of the couple of two-stage cylinders 108a and 108b of each moving block 105, is first actuated to ascend by 10 mm, one end side (right-hand side as illustrated) of the support plate 113 moves upward around the other end side (left-hand side). Specifically, the support plate 113 tilts, and the cap 23 that is grasped by the engaging members 121a and 121b is forced to tilt with respect to the normal line of the test tube 20. Thus, the cap 23 tilts from the opening of the tube 20 to establish a half-open state.

Then, if the other two-stage cylinder 108b is actuated to ascend by 10 mm, the left-hand side of the support plate 113 as illustrated moves upward around the right-hand side. Specifically, the support plate 113 tilts in a direction opposite to the aforesaid direction, and the cap 23 that is grasped by the engaging members 121a and 121b is forced to tilt on the opposite side with respect to the normal line of the test tube 20. Thus, the cap 23 can be removed through the opening of the tube 20.

Then, if the pair of two-stage cylinders 108a and 108b are simultaneously actuated to ascend by 40 mm, the support plate 113 ascends in a horizontal state, whereupon the cap 23 is pulled up and removed from the test tube 20. When the respective air cylinders 119 of the cap removal units 112 are simultaneously actuated to withdraw the piston rods 120, the engaging members 121a and 121b retract from the cap 23 of the test tube 20. Since the diameter of the cap 23 is larger than the space between the pair of cap guide members 117 at this point in time, the cap 23 abuts the guide members 117 and is disengaged from the pins 126 without following the retreat of the engaging members 121a and 121b as the engaging members 121a and 121b retreat. Since the cap 23 is pressed downward by the cap retaining pin 114 that is urged by the coil spring 115, moreover, it is recovered into a directly underlying cap recovery box 127 by the cap guide members 117.

When the removal of the respective caps of the first, third, and fifth test tubes 20-1, 20-3 and 20-5 as viewed in the conveying direction, among the five test tubes 20 supported by the test tube rack 19, is finished in the aforesaid manner, the remaining second and fourth test tubes 20-2 and 20-4 are uncapped. Thus, in the second stage of cap removal, the test tube rack 19 is stopped by the second rack stopper 75 when the second and fourth test tubes 20-2 and 20-4 are located in the cap removing position with the actuator bracket 79 advanced by the air cylinder 77.

The respective caps of the second and fourth test tubes 20-2 and 20-4 are removed in the same manner as those of the first, third, and fifth test tubes 20-1, 20-3 and 20-5. Since the first, third, and fifth test tubes are already uncapped so that their respective openings are opened, they may possibly be invaded by foreign matter when the second and fourth test tubes are uncapped. However, the three shutter cylinders 95 that adjoin the air cylinders 91 for advancing and retreating the clamping pieces 93 are actuated simultaneously. Thus, the respective piston rods 96 of the shutter cylinders 95 are actuated simultaneously with the air cylinders 91, so that the advanced shutters 97 cover regions around the opening portions including the respective top openings of the test tubes 20, thereby preventing invasion of foreign matter or the like through the openings of the tubes.

When the removal of the respective caps of the five test tubes 20 supported by the test tube rack 19 is completed, the rotary actuator 83 of the second rack stopper 75 is actuated to rock the stopper piece 86 through about 90 degrees, whereupon the gel tip 85 is retracted from the channel 34, as indicated by solid line in FIG. 11. Thus, the test tube rack 19 that supports the uncapped test tubes 20 is moved out into the stocker unit 13 by the rack conveying path 18.

According to this embodiment, caps on a plurality of test tubes that are held in a test tube rack conveyed along the rack conveying path can be removed simultaneously, so that the test tubes can be uncapped automatically and efficiently.

In the embodiment described above, the five test tubes 20 are held in each test tube rack 19, the first, third, and fifth test tubes 20 are uncapped in the first stage, and the remaining second and fourth test tubes 20 are uncapped in the second stage. However, this invention is not limited to the above-described number of test tubes 20 held in each test tube rack 19 and the alternate method of cap removal.

This invention is not limited directly to the embodiment described above, and its components may be embodied in modified forms without departing from the scope or spirit of the invention. Further, various inventions may be made by suitably combining a plurality of components described in connection with the foregoing embodiment. For example, some of the components according to the foregoing embodiment may be omitted. Furthermore, components according to different embodiments may be combined as required.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An automated test tube cap removal apparatus comprising:
   a cap remover having a cap removing position for a test tube which contains a specimen;
   a test tube rack which has a plurality of insertion holes for holding a plurality of capped test tubes upright in a row and loads the test tubes into the cap removing position;
   a clamping mechanism which is disposed in the cap removing position and clamps the plurality of test tubes in the test tube rack; and
   a cap removal unit disposed in the cap removing position and configured to move upward to remove caps from some of a plurality of test tubes held in every other of the plurality of insertion holes in a manner such that the caps are simultaneously supported by engagement and then move upward to remove caps from the remaining test tubes in a manner such that the caps are simultaneously supported by engagement,
   the cap removal unit including a pair of engaging members which are arranged at every other intervals of the plurality of insertion holes and are capable of advancing and retreating with respect to the caps and laterally clamping each cap when advanced, a lift mechanism which raises the pair of engaging members while alternately moving the engaging members upward, thereby removing the cap from each test tube, and a cap guide member which separates the cap from the engaging members and guides the cap for dropping when the engaging members retract from the cap after the cap removal,
   wherein the clamping mechanism is provided with a shutter, capable of advancing and retreating with respect to the test tubes in the test tube rack, and is configured to advance in association with an operation to clamp each test tube and cover an opening of each uncapped test tube by means of the shutter.

2. An automated test tube cap removal apparatus according to claim 1, wherein the cap removal unit performs two-action cap removal such that the caps of remaining two test tubes, among five test tubes held in the test tube rack, are removed after the caps of three test tubes, including two opposite side ones and a middle one, are removed.

3. An automated test tube cap removal apparatus according to claim 1, wherein the clamping mechanism is provided corresponding to the engaging members of the cap removal unit and is configured to clamp a test tube specified by the engaging members when the cap of the specified test tube is removed.

4. An automated test tube cap removal apparatus according to claim 1, wherein each said engaging member includes a needle pin to be thrust into the cap of each test tube.

5. An automated test tube cap removal apparatus comprising:
   a test tube rack loading unit for loading a test tube rack which holds a plurality of test tubes, which contain a specimen and individually have openings capped, upright in a row;
   a rack conveying path through which the test tube rack loaded from the test tube rack loading unit is conveyed in an arrangement direction of the test tubes;
   a clamping mechanism which is provided in the course of conveyance of the rack conveying path and simultaneously clamps respective trunks of a plurality of test tubes in a manner such that the test tube rack conveyed along the rack conveying path is temporarily stopped;
   a cap removal mechanism which is interlocked with the clamping mechanism and ascends in a manner such that caps of every other one of the plurality of test tubes clamped by the clamping mechanism are simultaneously supported by engagement, thereby removing the caps, and then ascends and removes the caps in a manner such that the remaining test tubes are simultaneously supported;
   a cap guide member which is interlocked with the cap removal mechanism and guides the removed caps for dropping; and
   a stocker unit which is located on the unloading side of the rack conveying path and stocked with the test tube rack which holds the uncapped test tubes,
   wherein the clamping mechanism is provided with a shutter, capable of advancing and retreating with respect to the test tubes in the test tube rack, and is configured to advance in association with an operation to clamp each test tube and cover an opening of each uncapped test tube by means of the shutter.

* * * * *